US012810985B2

(12) United States Patent
Bailey et al.

(10) Patent No.: US 12,810,985 B2
(45) Date of Patent: Nov. 24, 2026

(54) SYSTEM AND METHOD FOR PROGRAMMING AN INFUSION DEVICE

(71) Applicant: CAREFUSION 303, INC., San Diego, CA (US)

(72) Inventors: Richard Bailey, Basingstoke (GB); Samuel Garcia, Dos Hermanas (ES); Chris Vincent, London (GB); Anshul Shandillya, Limerick (IE)

(73) Assignee: CAREFUSION 303, INC., San Diego, CA (US)

( * ) Notice: Subject to any disclaimer, the term of this patent is extended or adjusted under 35 U.S.C. 154(b) by 531 days.

(21) Appl. No.: 18/286,543

(22) PCT Filed: Apr. 8, 2022

(86) PCT No.: PCT/US2022/024102

§ 371 (c)(1),
(2) Date: Oct. 11, 2023

(87) PCT Pub. No.: WO2022/221145

PCT Pub. Date: Oct. 20, 2022

(65) Prior Publication Data

US 2024/0189507 A1 Jun. 13, 2024

Related U.S. Application Data

(60) Provisional application No. 63/173,967, filed on Apr. 12, 2021.

(51) Int. Cl.

*G16H 20/17* (2018.01)
*G06F 3/04847* (2022.01)

(Continued)

(52) U.S. Cl.

CPC ......... *G16H 20/17* (2018.01); *G06F 3/04847* (2013.01); *G16H 20/10* (2018.01); *G16H 40/63* (2018.01); *A61M 2205/502* (2013.01)

(58) Field of Classification Search

None

See application file for complete search history.

(56) References Cited

U.S. PATENT DOCUMENTS

| | | | | |
|---|---|---|---|---|
| 8,682,042 B1 * | 3/2014 | Manion | G06Q 10/00 | 382/187 |
| 2004/0199215 A1 * | 10/2004 | Lee | G16H 20/30 | 607/48 |

(Continued)

FOREIGN PATENT DOCUMENTS

| | | |
|---|---|---|
| CN | 1618075 A | 5/2005 |
| CN | 1838972 A | 9/2006 |

OTHER PUBLICATIONS

International Search Report and The Written Opinion of the International Searching Authority for Application No. PCT/US2022/024102, dated Jun. 20, 2022, 13 pages.

(Continued)

*Primary Examiner* — Katheryn A Malatek
(74) *Attorney, Agent, or Firm* — MASCHOFF BRENNAN

(57) ABSTRACT

An infusion device determines, based on a medication loaded by the device, a number of digit fields for inputting a parameter associated with the medication, obtains first and second limits pertaining to the medication, determines which of the digit fields are selectable based on the first limit, displays, on a display screen, a plurality of selectable character input fields corresponding to the number of digit fields, visually identifies a first of the input fields as an adjustable field, displays one or more controls for incrementing or decrementing a value of the identified adjustable field, visually identifies, responsive to receiving the selection of a second character input field, the second character input field as the adjustable field and, in response to determining that an adjusted value exceeded the second limit, (Continued)

displays an alert proximate to the adjusted value of the second selectable character input field.

20 Claims, 10 Drawing Sheets

(51) Int. Cl.
*G16H 20/10* (2018.01)
*G16H 40/63* (2018.01)

(56) References Cited

U.S. PATENT DOCUMENTS

2006/0140798 A1* 6/2006 Kutsuzawa ....... A61M 5/16831 417/474
2007/0156624 A1* 7/2007 Palma .................... G16H 50/20 706/60
2007/0213598 A1* 9/2007 Howard ................ A61M 5/142 600/300
2008/0033749 A1 2/2008 Blomquist
2011/0066260 A1* 3/2011 Condurso .............. G16H 40/67 700/83
2011/0224523 A1 9/2011 Budiman
2013/0191770 A1 7/2013 Bartz et al.

OTHER PUBLICATIONS

Bd Switzerland Sari: "BO Alaris (TM) nexus GP Volumetric Pump Model: GPneXus1 en Directions for Use", Mar. 31, 2020 (Mar. 31, 2020), pp. 1-74, XP055927358, Retrieved from the Internet: URL:https ://manualzz.com/doc/55401060 [retrieved on Jun. 2, 2022].
Anonymous: "Spinbox (lv_spinbox)—LVGL documentation", , Oct. 28, 2020 (Oct. 28, 2020), pp. 1-7, XP055927335, Retrieved from the Internet: URL:https://web.archive.org/web/20201028150949/https://docs.lvgl.io/latest/en/html/widgets/spinbox.html [retrieved on Jun. 2, 2022].
Anonymous: "New object idea : number spin box . Issue #485 . lvgl/lvgl . GitHub", Feb. 1, 2019 (Feb. 1, 2019), pp. 1-4, XP055927355, Retrieved from the Internet: URL:https://github.com/lvgl/lvgl/issues/485 [retrieved on Jun. 2, 2022].
Chinese Office Action for Application No. 202280041439.1, dated Apr. 22, 2026, 17 pages including translation.
European Office Action for Application No. 22718553.5, dated Jun. 29, 2026, 6 pages.

* cited by examiner

SYSTEM AND METHOD FOR PROGRAMMING AN INFUSION DEVICE

CROSS-REFERENCE TO RELATED APPLICATION

This is a National Stage Application filed under 35 U.S.C. 371, of International Patent Application No. PCT/US2022/024102, filed on Apr. 8, 2022, which claims the benefit of U.S. Provisional Application No. 63/173,967, filed on Apr. 12, 2021, the entirety of each of which is incorporated herein by reference for all purposes.

TECHNICAL FIELD

The invention relates generally to systems and methods for programming medical devices.

BACKGROUND

Various medical devices and instruments typically found in a care providing institution are used to provide medication, monitor patient condition, and diagnose disease. Common to all of these devices is a need to enter therapeutic or patient-related values for various parameters that are used either to program the identification of the device or provide identification or other needed information that are then used by a computer-controlled system, which may be ward-based or institution wide, to monitor and record diagnoses and treatment related to a particular patient.

One example of a medical device where the input of relatively high numbers of parameter values is required is an infusion device, or pump; an apparatus for administering medication to a patient. An infusion pump can be used to administer drugs to a patient in small, carefully measured doses at frequent intervals or, with some devices, slowly and continuously. Infusion pumps are typically provided with a control panel or buttons for the user to program the desired infusion. The user can typically input the drug to be infused, the syringe brand and size and the desired infusion rate or duration of infusion. The device is also provided with a display which firstly allows an operator to view his or her inputs from the control panel as he or she programs the pump, and also provides information to the operator whilst infusion is in progress.

As availability of drugs, therapeutic techniques, and technological capability have improved, the demand for sophistication in drug delivery has increased. In many instances, this added sophistication results in more complicated infusion pump operation. Achieving this sophistication in drug delivery capability while maintaining ease of use has been a major challenge for infusion pump manufacturers.

As the sophistication of the available infusion pumps has increased, so too have the number of parameters that may be used to control the infusion. Typically, an infusion pump comprises a pumping element that causes a precisely measured flow of fluid to be infused to the patient. This pump element is controlled by a processor that generally has a programmable memory associated with it for storing instructions to be used by the processor to control the infusion. The sophistication of currently available infusion pumps with programmable processors and extensive memory capabilities for controlling complicated drug delivery schemes adds significantly to the choices available to a physician for prescribing a drug regimen to be infused.

The range of possible infusion parameters includes, but is not limited to, infusion rate, infusion duration, dose volume, lockout period, repeat period, bolus size, bolus rate, patient weight, syringe size, container volume, security codes, drug units (e.g. milligrams), drug concentration, concentration units, or pharmacokinetic parameters. Each of these parameters may be entered by a user into the memory of the pump using in input device such as a keypad connected directly to the pump. Alternatively, the pump may be programmed by commands received over a network or other communication scheme from a central computer, handheld device, or other data transfer system or device.

Because of the large number of therapeutic modalities and the extensive number of possible required parameters, manufacturers have been challenged to provide a user interface that assists the user in entering desired parameters by accelerating the entry process as much as possible while at the same time, simplifying the process.

One attempt to save time when entering infusion parameters involved programming the infusion pump with an automatic repeat function, whereby pressing and holding any one of the scroll keys depressed causes the display to repeatedly increase or decrease until the scroll key is released. The repeat rate can also be changed depending on the amount of time the scroll key is pressed. For example, depressing the scroll key for several seconds may increase the repeat rate according to a function, which may be linear, or some other function, such as logarithmic. However, such prior systems may be disadvantageous in that the user may inadvertently scroll past the desired value by a large amount before releasing the scroll key. In other instances, the user may undershoot the desired value by releasing the scroll key too early. In either case, any potential savings in time that might have accrued from use of such a system may be lost.

Hence, those skilled in the art have recognized a need for a system and method of data input that is convenient, easy to use, and requires no additional scroll keys or other input controls, yet provides a user with an easily controlled ability to scroll through an extensive set of values, whether numerical, character or text based, that decreases data entry time and difficulty. This invention fulfills these and other needs.

SUMMARY

The subject technology described herein addresses the problems with existing methods for programming infusion devices by providing an interface for rapid programming of infusion parameters. In this regard, the subject technology is directed to, according to various aspects, an infusion device, comprising: an infusion pump; a processor; a memory device; and a display screen. The processor is configured to: by the infusion pump; determine, based on determining the medication, a number of digit fields for inputting a parameter associated with the determined medication; query a dataset for limits pertaining to the medication; obtain, from the dataset based on the querying, a first limit and a second limit pertaining to the medication; determine which of the digit fields are selectable based on the first limit; display, on the display screen of the infusion device, a plurality of selectable character input fields corresponding to the number of digit fields determined to be selectable; visually identify, on the display screen, a first character input field of the displayed selectable character input fields as an adjustable field; display, on the display screen, one or more controls for incrementing or decrementing a value of the identified adjustable field, each control configured to only increment or decrement the value of the identified adjustable field; receive a selection of a second character input field of the displayed selectable character input fields; visually identify, on the display screen, after (e.g., responsive to) receiving the selection, the second character input field as the adjustable field; adjust a value of the selected second character input field based on an activation of the one or more controls while the second character input field is selected as the adjustable field; determine that the adjusted value of the second character input field exceeded the second limit; and in response to determining that the adjusted value exceeded the second limit, display an alert, indicating the adjusted value exceeded the second limit, proximate to the adjusted value of the second selectable character input field. Other aspects include corresponding systems, methods, apparatuses, and computer program products for implementation of the foregoing features.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE FIGURES

The accompanying drawings, which are included to provide further understanding and are incorporated in and constitute a part of this specification, illustrate disclosed embodiments and together with the description, serve to explain the principles of the disclosed embodiments. In the drawings.

DESCRIPTION

The disclosed methods and system provide for the programming of infusion devices.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

Figure 1:
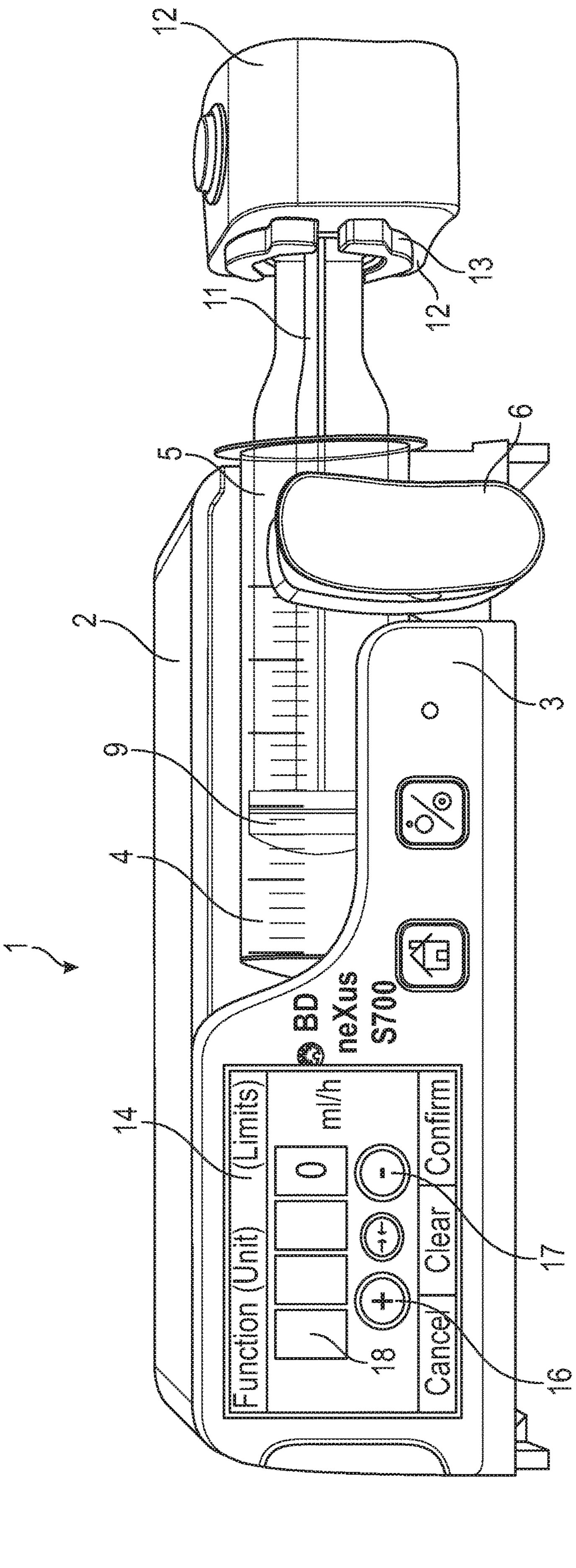
FIG. 1 depicts an example syringe pump, according to various aspects of the subject technology.

FIG. 1 depicts an example infusion device 1, according to various aspects of the subject technology. Infusion device 1 includes a housing 2 having a syringe cradle 3 therein which is of appropriate size for receiving a syringe 4, in particular the syringe barrel 5 thereof. While the depicted infusion device 1 includes a syringe pump, other types of infusion devices are also contemplated. For example, infusion device 1 may includes a peristaltic pump that drives a fluid through an intravenous (IV) tube.

In the example shown, there is a clip 6 provided to support the syringe barrel 5 in the syringe cradle 3 and a groove which receives the flange 7 of the syringe barrel 5. The prior art syringe pump 1 as shown is in a state either before or during infusion where the syringe plunger 8 is extended out of the syringe barrel 5. The syringe plunger 8 terminates with a syringe piston 9 at one end, which forces fluid from the syringe 4 and a syringe flange 10 at an opposing end, connected by the syringe plunger stem 11. The syringe flange 10 is pushed via the driver head 12 when in use, which forces the syringe piston 9 through the syringe barrel 5 thereby forcing liquid through the end of the syringe 4. The syringe flange 10 may additionally be supported or clamped by one or more retaining arms 13.

As well as operating buttons or switches, which the operator uses to activate and program the syringe pump 1, there is a display screen 14. The display screen 14 may be a simple LCD (liquid crystal display) having a small number of segments, for example seven segments in a figure-of-eight configuration per character, adapted to display a small number of alphanumeric characters. The display may be monochromatic, for example, it might only display red, green or grey/black characters. Alternatively, the display 14 might be a more complicated liquid crystal display capable of displaying more characters or more complicated characters. The LCD may be backlit, for example, using light emitting diodes (LEDs). In some implementations, the infusion pump may include a TFT LCD. A TFT is a thin-film transistor-based LCD technology. In some implementations, the display screen 14 is also a touchscreen such as a capacitive or resistive touchscreen.

When programming an infusion device, the user must input the type of syringe 4 being fitted to the pump. The pump stores in an internal memory a database of known syringe types containing information such as syringe diameter and stroke. The infusion pump firmware calculates the position of the syringe plunger and syringe piston based on movement of the syringe driver head and the type and size of the syringe. This allows the machine to display the calculation of volume infused, time elapsed, volume remaining and time remaining. As infusion continues and the driver head moves, these calculations can be updated, and the displayed information changed.

Infusion device 1 may be provided with a scrolling system comprising an "up" scroll key and a "down" scroll key which are operable to increase or decrease pumping parameters, such as the mass flow rate setting shown on a display, or the VTBI (volume to be infused) setting shown on the display. In some cases, each scroll key may be labeled with upward 16 and downward 17 symbols or chevrons. Pressing either of the keys causes the display to scroll numerically upwardly or downwardly.

For example, assuming that the display shows "6", pressing the chevron UP key causes the display to scroll up by one unit at a time to show "7", "8", "9", "10", "11", and so on. The display may be caused to scroll up in one unit increments (e.g. 1 ml) until "20" and then may automatically switch to scroll up further in ten unit increments until it reaches, for example, a display of "200", where after continued pressing of the chevron UP key may cause the display to increase in hundred unit increments to show "300", "400", and so on. When the display reaches a certain number, such as "700", pressing the chevron UP key may cause the display to move again in single increments, such as "701", "702", "703", and so on. The same or similar scheme may be performed when decrementing using the DOWN key 17 (in reverse).

Display screen 14 may be used for inputting parameters, or to enter data for use by the device 1 in monitoring and recording the status or condition of a patient or a course of treatment. For example, a processor of pump 1 (FIG. 7) may communicate infusion parameters input by a user to a pump controller (not shown). Display panel 14 may be configured to show four character or digit fields 18. Of course, the display may be configured to show more than four fields, so as to accommodate inputting numerical values greater than "9999" or less than "−9999", or numerical values having an accuracy greater than five or more significant digits, such as "1.0001". As will be described further, display panel 14 may further include a focus indicator designating a field 18 selected for input. The focus indicator is useful in that it identifies which digit or character field 18 displayed on display 14 that is active, that is, can be changed using the controls of the device or by touching a displayed character field 18. The term character field and digital field are used synonymously herein.

The UP key 16 and DOWN key 17 may be touch elements on display screen 14, as depicted, or may be physical switches, such as bubble-style or membrane switches. Such keys are displayed as needed depending on the configuration and programming of the infusion pump or medical device. Other types of keys or icons, apart from the UP and DOWN keys illustrated in FIG. 1 may be used in order to change the value shown on the display 14. For example, track balls, joysticks, touch pads, and scroll wheels may be used for scrolling the displayed value either upwards or downwards.

Figure 2B:
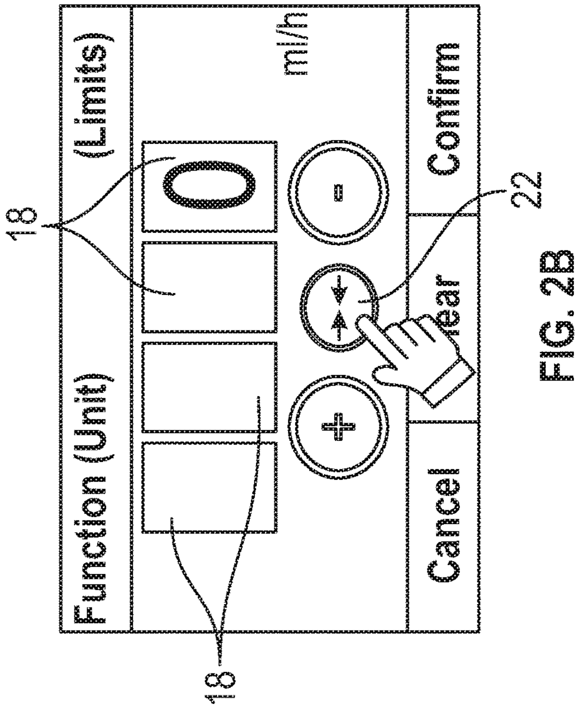
FIGS. 2A, 2B, and 2C depict an example touch-sensitive display screen for an accelerated input of parameters, according to various aspects of the subject technology.
Figure 2A:
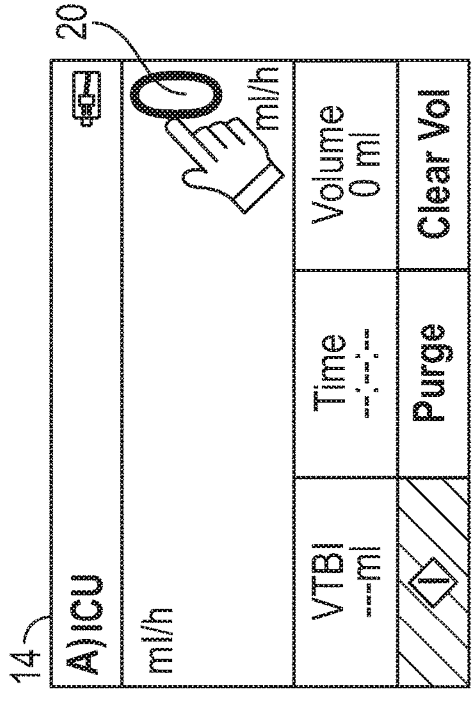
Figure 2C:
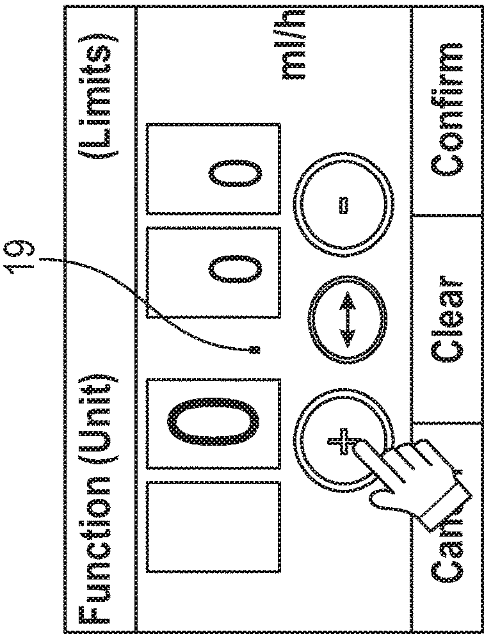

FIGS. 2A, 2B, and 2C depict an example touch-sensitive display screen 14 for an accelerated input of parameters, according to various aspects of the subject technology. For the purposes of the depicted example, a medication is presumed loaded into the device as shown in FIG. 1, and the device is capable of determining the medication type, for example based on a previous scanning of the medication identifier or selection at display screen 14. FIG. 2A depicts initiating an input of parameters using touch-sensitive display screen 14. A user simply touches the displayed default digit to initiate programming of the device. On receiving the touch input, the device determines a medication loaded by the infusion pump and selects a number of input fields 18 for inputting a parameter associated with the determined medication. In the depicted example, the number of digits is four.

According to various implementations, the number of character fields may be determined by querying a database for limits associated with the medication. The device may obtain, from a dataset returned from the database, a dosage unit and a first limit and a second limit pertaining to the medication. The first limit may be an upper bound (e.g. maximum limit) on the dosage unit. In some implementations, the dataset may indicate a default parameter (at the dosage unit). Based on information in the returned dataset, including the limit(s), the device may determine which of the input digit fields are selectable and display selectable parameter input characters corresponding to the number of input digits determined to be selectable. In FIG. 1, four character fields 18 are displayed. As depicted in FIG. 2A, the character fields 18 may not be displayed until a displayed default character 20 is selected, thereby causing display screen 14 to switch to displaying the number of designated character fields, as shown in FIGS. 1, 2B, and 2C.

According to various implementations, display screen 14 may display a decimal selector 22, as shown in FIG. 2B The user may select decimal selector 22 to display (if available) a decimal character and character fields 18 for smaller increments below a single unit value, as shown in FIG. 2C. Accordingly, the displayed character fields 18 may separate according to a predetermined pattern for the determined medication. For example, if the limit(s) returned in the dataset indicate that the decimal locations should be hundreds, the right side of character fields 18 may include two character fields 18, and the left side of display screen 14 may also display two character fields. However, if the maximum limit is a single digit and the resolution is in the thousandths then one field 18 may be displayed on the left portion of display screen 14, followed by a decimal, followed by three fields 18 on the right portion of display screen 14.

In the depicted example, decimal selector 22 includes graphic arrow indicators pointing inward toward each other while the character fields are not separated, and changes to pointing outward away from each other when the character fields are separated by a decimal. Repeated toggling of decimal selector 22 may toggle between predetermined field layouts; e.g. from two fields one each side, to one/three, to four uniform fields without a decimal. In some implementations, the same number may be represented in the display, but with toggling selecting between greater or lesser resolutions above or below the decimal (see e.g. FIGS. 3A, 3B, and 3C).

Figure 3A:
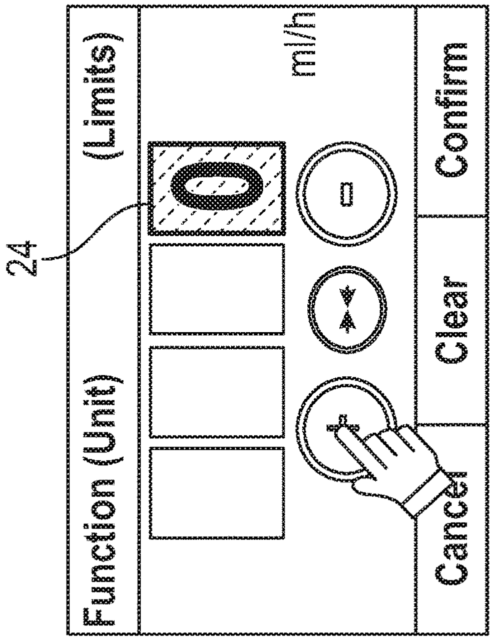
FIGS. 3A to 3D depict various display screens with a visible focus indicator being displayed at a selected character field, according to various aspects of the subject technology.

FIGS. 3A to 3D depict various display screens with a visible focus indicator being displayed at a selected character field 18, according to various aspects of the subject technology. FIG. 3A depicts a focus indicator 24 highlighting the least significant digit. When a character field 18 is selected, the character field is highlighted. In this regard, the highlighted field visually identifies the adjustable input character, with the highlighted area enclosing only the adjustable input character. When a scroll key 16, 17 is selected the value of the highlighted character will change.

Figure 3B:
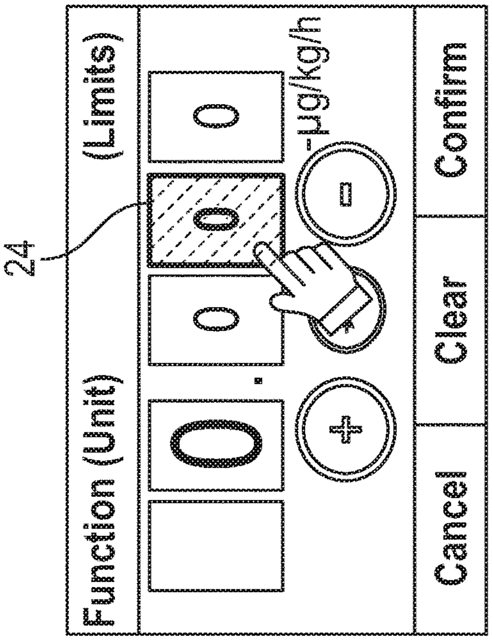
Figure 3C:
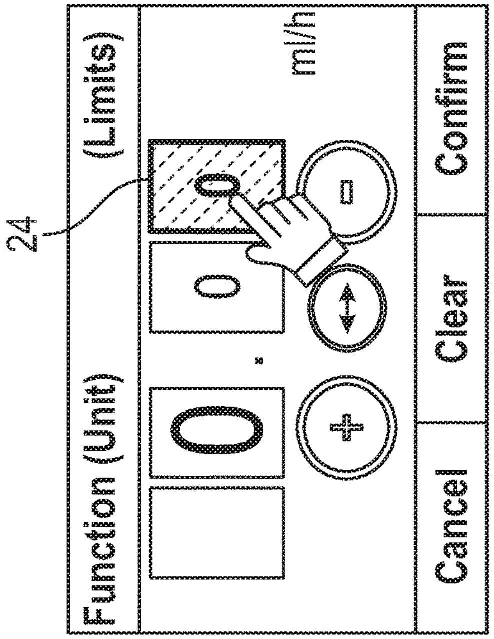

FIGS. 3B and 3C depict example selections of different character fields and providing a focus indicator 24 corresponding to the selections. In the depicted examples, the user has selected a character field below the decimal or below a single unit value.

Figure 3D:
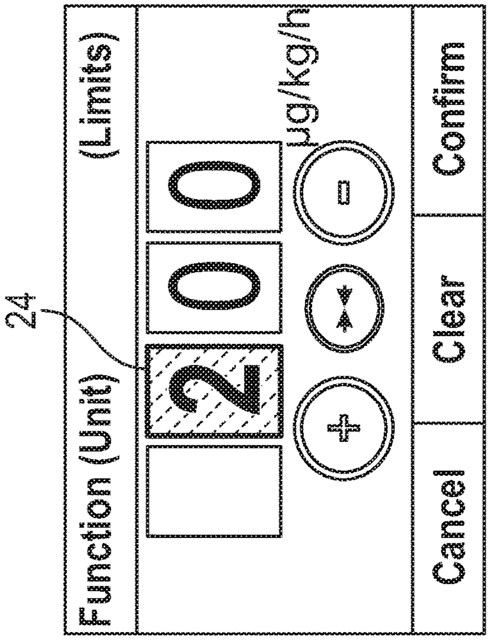

FIG. 3D depicts an example alert responsive to a user selection of an out-of-range digit field, according to various aspects of the subject technology. In some implementations, device 1 may change a background color of the display screen 14 responsive to obtaining the first limit and the second limit. In some implementations, the change to the background color may be responsive to selection of an editable field 18 that is out of range or incrementing the field to a value that is out of range.

In the illustrated examples, the focus indicator 24 is visual, appearing to highlight the entire character input field 18, which may appear as a text box. As stated above, the focus indicator 24 identifies that digit or character that will be changed when the user presses either the UP key 16 or the DOWN key 17. For example, in FIG. 3A, the focus indicator 24 is positioned at the ones digit 18 at the far right of the display 14. Thus, the displayed numerical value will increase by an increment of one when the UP key 16 is pressed and will decrease by the same increment when the DOWN key 17 is pressed.

The processor of device 1 (see FIG. 7) tracks the numerical value shown on the display 14, and depending on that numerical value, may adjust the position of the focus indicator 24 shown on the display 14. For example, pressing the UP key 16 causes the ones digit 18 to increment upwards. When it reaches "9", the processor can be controlled to automatically shift the focus indicator to the left so that it appears under the tens digit when the UP key 17 is pressed the next time. As such, the focus indicator may also appear highlight the tens digit or hundreds digit. In other embodiments, the processor may be programmed to keep the focus indicator located under the ones digit and display a "0" when the UP key is pressed a further time.

Other visual cues may be used as an alternative to or in combination with the highlighting of the digit field to indicate a changeable digit associated with the UP and DOWN keys 16, 17. Non-limiting examples of such focus indicators include, for example, displaying the changeable digit at a distinct brightness or intensity, or color displaying the changeable digit in a larger size than non-changing digits, or displaying a cursor, pointer, or other graphical icon that in some way points out to a user which digit will be changed upon a key press. In some implementations, the focus indicator may underline the digit field(s).

Figure 4A:
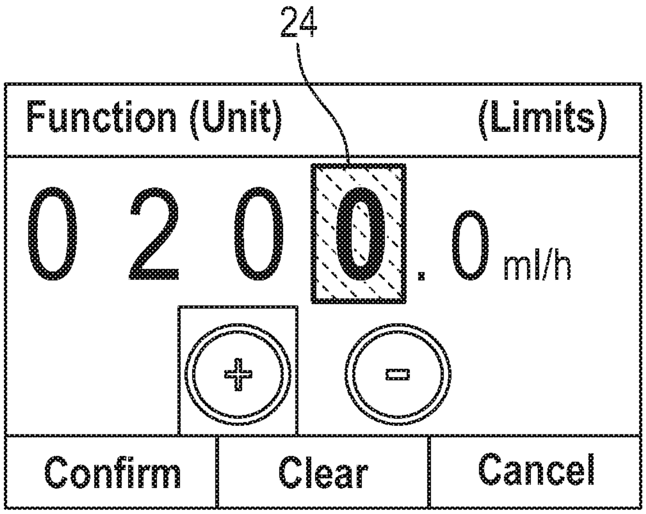
FIGS. 4A and 4B depicts an example display screen in which two character fields are highlighted, according to various implementations of the subject technology.
Figure 4B:
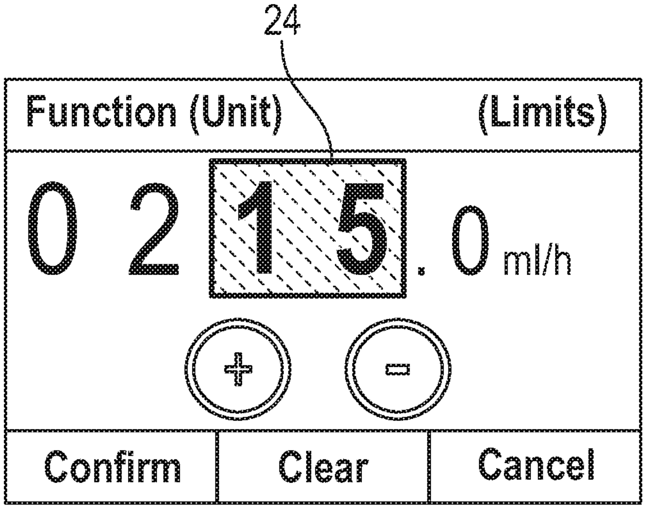

FIGS. 4A and 4B depicts an example display screen in which two character fields are highlighted, according to various implementations of the subject technology. In some implementations, as depicted in FIGS. 4A and 4B, the focus indicator 24 may grow to encompass two or more characters, depending on the permissible range of the dataset for the medication. For example, device 1 may receive an adjustment of a current value of the adjustable input character 18 to a higher value and, after (e.g., responsive to) the adjusted current value exceeds a threshold for a display of a single digit representation of the adjusted current value, display screen 14 may expand the highlighted area to enclose the adjustable input character and an adjacent input character of the displayed selectable parameter input characters to represent the adjusted current value. Similarly, device 1 may receive an adjustment of the adjusted current value of the adjustable input character to a lower value and, responsive to the adjusted current value being reduced below the threshold for a display of the single digit representation, display screen 14 may revert the highlighted area to enclose only the adjustable input character.

According to various implementations, when a character field 18 is selected and highlighted by a focus indicator 24, the processor of device 1 (FIG. 10) may begin to monitor controls 16 and 17. If activation of one of the controls is not received during a period of time then display screen 14 may begin to flash the corresponding focus indicator. If no further input is received after a second period of time, then the corresponding focus indicator 24 may be removed (removing the highlighted portion of the display). In some implementations, the value may revert to a default value.

Figure 5B:
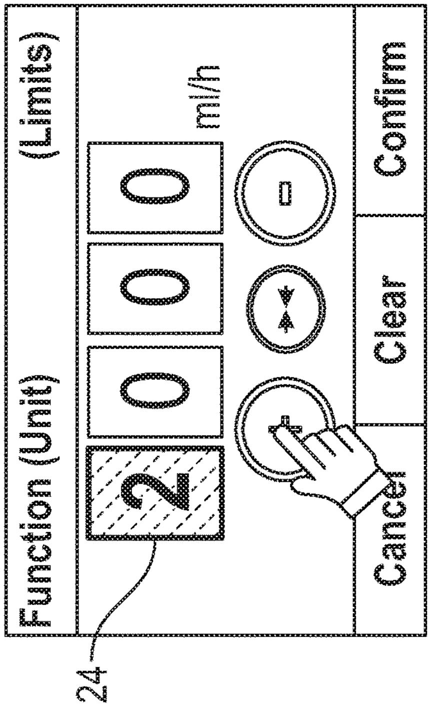
FIGS. 5A to 5C depict an accelerated value input based on selection of a most significant digit field, according to various aspects of the subject technology.
Figure 5C:
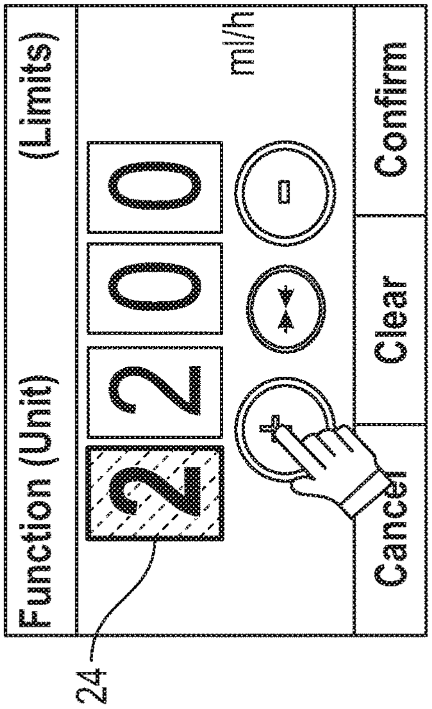
Figure 5A:
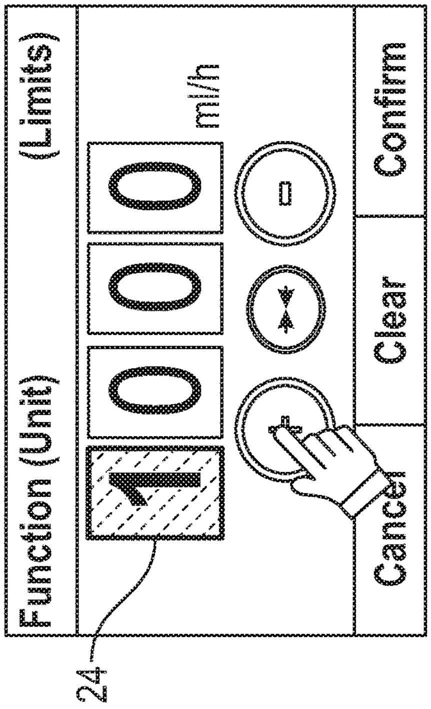

FIGS. 5A to 5C depict an accelerated value input based on selection of a most significant digit field, according to various aspects of the subject technology. According to various implementations, a selection of a higher significant digit field will result in the value being incremented by the magnitude of the field. For example, as depicted in FIGS. 5A and 5B, a user may select the thousandths digit, and activation of the UP key 16 results in an immediate increment by "1000". Depending on the limit(s) returned in the dataset, further increments beyond a predetermined threshold may be reduced to the next lowest significant digit. For example, if the upper limit on the value is "2800" then further selection of UP key 16 may increment subsequent values by "100" or "200", or a certain percentage of the selected field, thereby providing a more reasonable solution than incrementing to a value that is outside of the limit. In the depicted example, further incrementing beyond "2000" results in an increase of "200", as depicted in FIG. 5C, or ten percent of the magnitude of the selected character field 18.

Accordingly, the value of a selected character input field on the left of the display may be greater than a value of an adjacent character input field to the right of the field by a magnitude of ten. The first and second character input fields may be null prior to the selected second character input field being adjusted. In the depicted example, adjusting the value of the second character input field includes setting the second character input field to "1" and the first character input field to "0" (from null). The value of the selected character input field is incremented responsive to each subsequent selection of activation of the UP key 16 until a first limit, after which each subsequent selection increments the first character input field up until a second limit (the second limit being greater than the first limit).

According to some implementations, a user may select a certain character field. For example, a user may select the tens field. If the user continues to press and activate the UP key 16, the tens digit 38 continues to increase. When the numerical value transitions from "790" to "800", the focus indicator 24 up-shifts a second time, moving from the tens digit to the hundreds digit 40. Continued pressing and activation of the UP key results in the displayed value increasing by increments of one hundred. The focus indicator may not move from the hundreds digit to the thousands digit 41 when the display shows "1000". The absence of an up-shift at "1000" is desirable in applications of the system where the maximum allowed input value is near "1000" or "2000", or if the desired input value rarely exceeds "1000" or "2000". In such applications, an up-shift at "1000" may cause the user to overshoot the desired input value. The system may be configured to up-shift to the thousands digit depending on the type of parameter being input or depending on the preferences or criteria programmed into the system by the institution or user.

Figure 6:
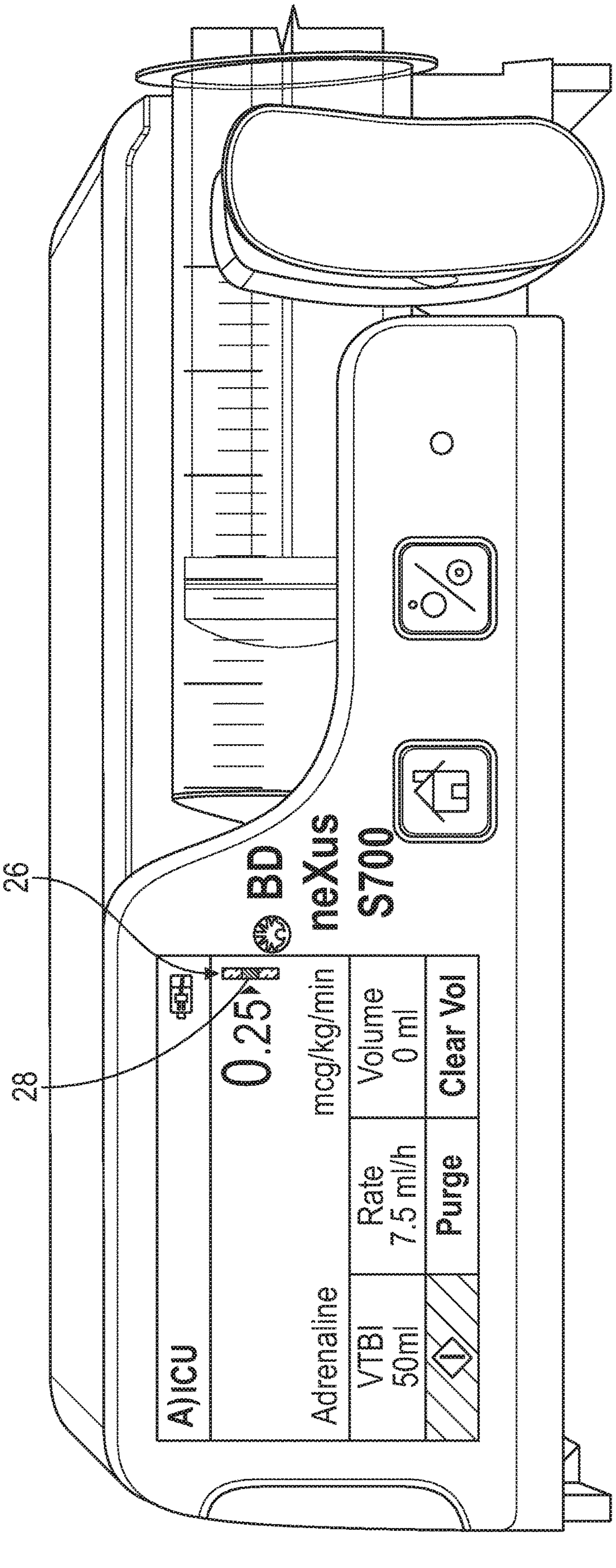
FIG. 6 depicts an example syringe pump including a display screen that depicting a limit indicator, according to various aspects of the subject technology.

FIG. 6 depicts an example syringe pump 1 including a display screen 14 that depicting a limit indicator, according to various aspects of the subject technology. The processor of device 1 may be configured to display, proximate to the plurality of selectable parameter input characters 18, a graphical representation of a parameter range 26 corresponding to the limit(s) received in the dataset. Range 26 may include a level indicator 28 that indicates where the current parameter sits within the range.

Figure 7:
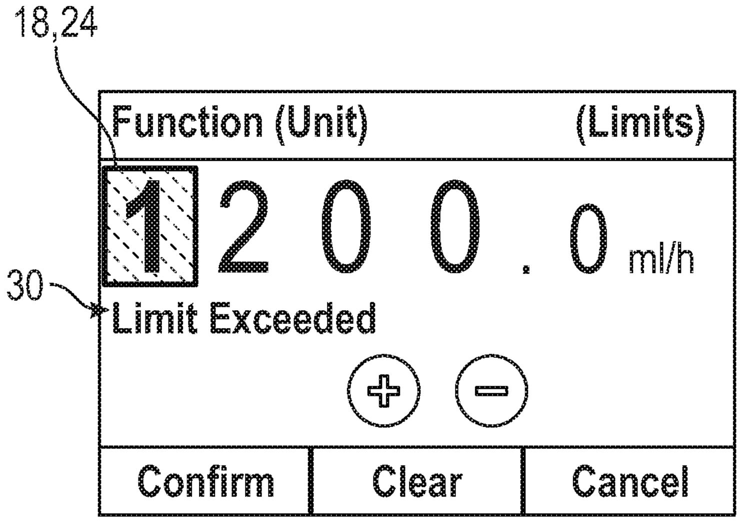
FIG. 7 depicts an example display screen depicting an alert indicator, according to various aspects of the subject technology.

FIG. 7 depicts an example display screen 14 depicting an alert indicator 30, according to various aspects of the subject technology. The processor of device 1 may be configured to display, proximate to the plurality of selectable parameter input characters 18, a graphical representation of an alert 30 corresponding to a limit being exceeded. In some implementations, the processor of device 1 may determine that an adjusted value of the selectable input character field 18 has exceeded a limit and, in response, display an alert indicator 30 indicating the adjusted value exceeded the limit. In some implementations, alert indicator 30 may be displayed proximate to the currently adjusted value. For example, alert indicator 30 may be displayed underneath and aligned with the currently adjusted value, as depicted in FIG. 7.

Figure 8:
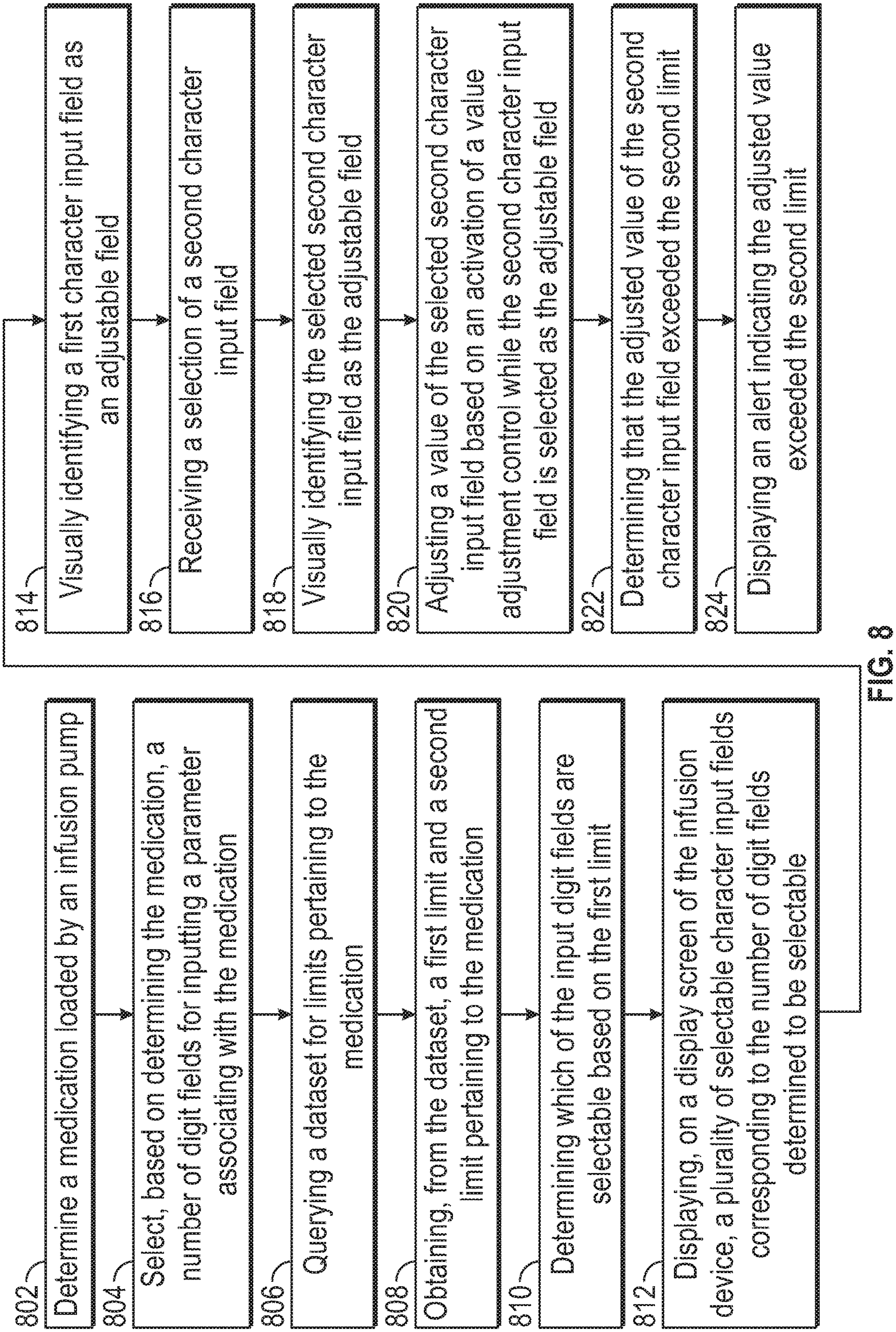
FIG. 8 depicts an example process flow for programming an infusion device, according to aspects of the subject technology.

FIG. 8 depicts an example process flow 800 for programming an infusion device, according to aspects of the subject technology. For explanatory purposes, the various blocks of example process 800 are described herein with reference to FIGS. 1 to 7, and the components and/or processes described herein.

The disclosed system generally relates to an infusion device with a programmable interface. According to various implementations, the infusion device includes a pump, a processor, a memory, and a display screen.

In the depicted example, the processor determines a medication loaded by an infusion device (802). Determining the medication may include receiving information from a scanner operably connected to the infusion device, including an identification and/or a type of the medication. For example, the identification and/or type of the medication may be obtained by scanning an RFID tag or barcode affixed to a packaging of the medication.

Based on determining the medication, the number of digit fields for inputting a parameter associated with the determined medication is determined (804). The number may have been included in the scanned information, or may be determined based on obtaining information from a database using the medication identifier (e.g., in a memory 356 or 358 of the infusion device or in a server 330). For example, the information may be preprogrammed in the pump, and/or may include a range of potential values for the medication, and the number of digits may be selected to accommodate values within the preprogrammed range.

A dataset is queried for limits pertaining to the medication (806). As described previously, a database may be queried for information pertaining to the medication. The database may be a dataset stored on the infusion device, or may be stored remotely by a server (e.g., in database 337 associated with a server 330). When the identity of the medication is known, the identity may be used to query the dataset for limits on the medication. The query may also include querying the dataset for a particular patient or patient condition. In this regard, the query request may be for limits on a certain medication for a certain medical condition, or for a patient with certain characteristics or of a certain demographic.

The infusion device obtains, from the dataset based on the querying, a first limit and a second limit pertaining to the medication (808). According to various implementations, the dataset may return one or more limits depending on, for example, the medication, a medical condition of the patient, and/or provided characteristics or demographic. The first and second limits may be an upper and lower limit respectively. Additionally, or in the alternative, the first and second limits may include a hard limit and a soft limit. For example, the hard limit may be a maximum (or minimum) possible limit on a dosage or rate of the medication, and the soft limit may be a threshold (maximum or minimum) limit on the dosage or rate in which an alarm may be raised by the device.

The processor determines which of the digits are selectable based on the first limit (810). For example, if a maximum value of the programmed rate is 2500 ml/hr then the processor may determine that all four digits are selectable. On the other hand, if the maximum value is "1000" ml/hr then the processor may determine that three digits are selectable, allowing the user only to reach the maximum amount by increasing the value via UP key 16.

The display screen 14 of the infusion device displays a plurality of selectable character input fields corresponding to the number of digits determined to be selectable (812), and visually identifies a first character input field 18 of the displayed selectable character input fields as an adjustable field (814). As described previously, a focus indicator 24 may identify the adjustable input character by highlighting an area enclosing only the adjustable input character.

One or more controls 16, 17 for incrementing or decrementing a value of the identified adjustable field are also displayed on the display screen. Each control may be configured to only increment or decrement the value of the identified adjustable field.

During use, display screen 14 (or processor) receives a selection of a second character input field of the displayed selectable character input fields (816) and visually identifies, responsive to receiving the selection, the second character input field as the adjustable field (818). In this regard, as a user selects a different character field 18 the newly selected field is identified with a focus indicator 24.

A value of the selected second character input field is adjusted based on an activation of the one or more controls while the second character input field is selected as the adjustable field (820). Processor is then configured to monitor the input against the received limits. In the depicted example, processor may determines that the adjusted value of the second character input field exceeded the second limit (822) and, in response to determining that the adjusted value exceeded the second limit, displays an alert indicating the adjusted value exceeded the second limit (824). The alert may be displayed proximate to the adjusted value of the second selectable character input field.

Many of the above-described examples of FIG. 8, and related features and applications, may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Figure 9:
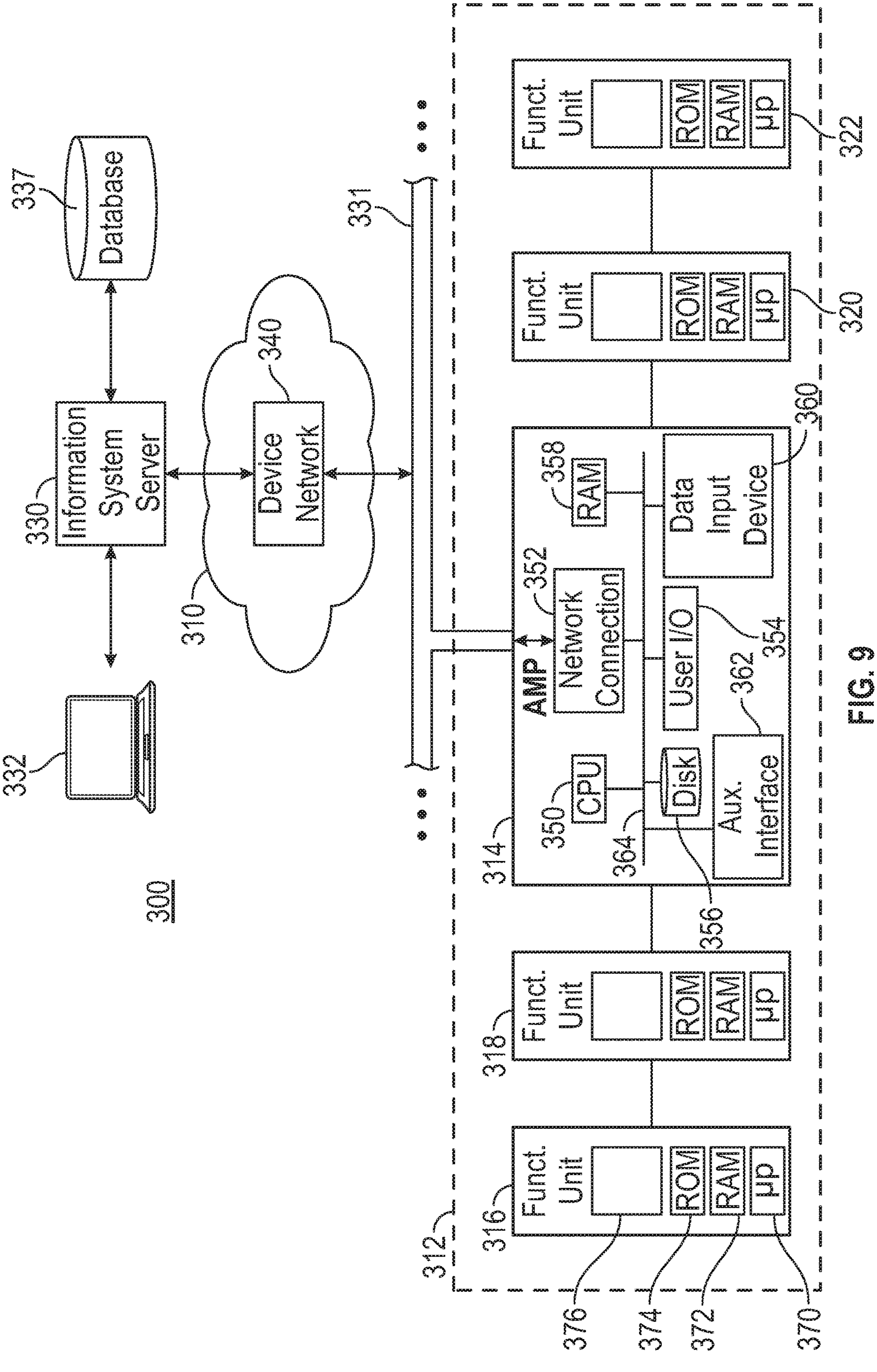
FIG. 9 depicts an example diagram of an institutional patient care system of a healthcare organization, according to aspects of the subject technology.

FIG. 9 depicts an example of an institutional patient care system 300 of a healthcare organization, according to aspects of the subject technology. In FIG. 9, a patient care device (or "medical device" generally) 312 is connected to a hospital network 310. The term patient care device (or "PCD") may be used interchangeably with the term patient care unit (or "PCU"), either which may include various ancillary medical devices such as an infusion pump, a vital signs monitor, a medication dispensing device (e.g., cabinet, tote), a medication preparation device, an automated dispensing device, a module coupled with one of the aforementioned (e.g., a syringe pump module configured to attach to an infusion pump), or other similar devices. According to some implementations, patient care device 312 may be representative of the previously described infusion device 1.

Patient care device 312 may be connected to an internal healthcare network 310 by a transmission channel 331. Transmission channel 331 is any wired or wireless transmission channel, for example an 802.11 wireless local area network (LAN). In some implementations, network 310 also includes computer systems located in various departments throughout a hospital. For example, network 310 of FIG. 3 optionally includes computer systems associated with an admissions department, a billing department, a biomedical engineering department, a clinical laboratory, a central supply department, one or more unit station computers and/or a medical decision support system. As described further below, network 310 may include discrete subnetworks. In the depicted example, network 310 includes a device network 340 by which patient care devices 312 (and other devices) communicate in accordance with normal operations.

Additionally, institutional patient care system 100 may incorporate a separate information system server 330, the function of which will be described in more detail below. Moreover, although the information system server 330 is shown as a separate server, the functions and programming of the information system server 330 may be incorporated into another computer, if such is desired by engineers designing the institution's information system. Institutional patient care system 300 may further include one or multiple device terminals 332 for connecting and communicating with information system server 330. Device terminals 332 may include personal computers, personal data assistances, mobile devices such as laptops, tablet computers, augmented reality devices, or smartphones, configured with software for communications with information system server 330 via network 310.

Patient care device 312 includes a system for providing patient care, such as that described in Eggers et al., which is incorporated herein by reference for that purpose. Patient care device 312 may include or incorporate pumps, physiological monitors (e.g., heart rate, blood pressure, ECG, EEG, pulse oximeter, and other patient monitors), therapy devices, and other drug delivery devices may be utilized according to the teachings set forth herein. In the depicted example, patient care device 312 comprises a control module 314, also referred to as interface unit 314, connected to one or more functional modules 316, 318, 320, 322. Interface unit 314 includes a central processing unit (CPU) 350 connected to a memory, for example, random access memory (RAM) 358, and one or more interface devices such as user interface device 354, a coded data input device 360, a network connection 352, and an auxiliary interface 362 for communicating with additional modules or devices. Interface unit 314 also, although not necessarily, includes a main non-volatile storage unit 356, such as a hard disk drive or non-volatile flash memory, for storing software and data and one or more internal buses 364 for interconnecting the aforementioned elements.

In various implementations, user interface device 354 is a touch screen for displaying information to a user and allowing a user to input information by touching defined areas of the screen. Additionally, or in the alternative, user interface device 354 could include any means for displaying and inputting information, such as a monitor, a printer, a keyboard, softkeys, a mouse, a track ball and/or a light pen. Data input device 360 may be a bar code reader capable of scanning and interpreting data printed in bar coded format. Additionally or in the alternative, data input device 360 can be any device for entering coded data into a computer, such as a device(s) for reading a magnetic strips, radio-frequency identification (RFID) devices whereby digital data encoded in RFID tags or smart labels (defined below) are captured by the reader 360 via radio waves, PCMCIA smart cards, radio frequency cards, memory sticks, CDs, DVDs, or any other analog or digital storage media. Other examples of data input device 360 include a voice activation or recognition device or a portable personal data assistant (PDA). Depending upon the types of interface devices used, user interface device 354 and data input device 360 may be the same device. Although data input device 360 is shown in FIG. 3 to be disposed within interface unit 314, it is recognized that data input device 360 may be integral within a pharmacy system or located externally and communicating with pharmacy system through an RS-232 serial interface or any other appropriate communication means. Auxiliary interface 362 may be an RS-232 communications interface, however any other means for communicating with a peripheral device such as a printer, patient monitor, infusion pump or other medical device may be used without departing from the subject technology. Additionally, data input device 360 may be a separate functional module, such as modules 316, 318, 320 and 322, and configured to communicate with controller 314, or any other system on the network, using suitable programming and communication protocols.

Network connection 352 may be a wired or wireless connection, such as by Ethernet, WIFI, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 316, 318, 320, 322 are any devices for providing care to a patient or for monitoring patient condition. As shown in FIG. 3, at least one of functional modules 316, 318, 320, 322 may be an infusion pump module such as an intravenous infusion pump for delivering medication or other fluid to a patient. For the purposes of this discussion, functional module 316 is an infusion pump module. Each of functional modules 318, 320, 322 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor or an intracranial pressure monitor or the like. Functional module 318, 320 and/or 322 may be a printer, scanner, bar code reader or any other peripheral input, output or input/output device.

Each functional module 316, 318, 320, 322 communicates directly or indirectly with interface unit 314, with interface unit 314 providing overall monitoring and control of device 312. Functional modules 316, 318, 320, 322 may be connected physically and electronically in serial fashion to one or both ends of interface unit 314 as shown in FIG. 3, or as detailed in Eggers et al. However, it is recognized that there are other means for connecting functional modules with the interface unit that may be utilized without departing from the subject technology. It will also be appreciated that devices such as pumps or patient monitoring devices that provide sufficient programmability and connectivity may be capable of operating as stand-alone devices and may communicate directly with the network without connected through a separate interface unit or control unit 314. As described above, additional medical devices or peripheral devices may be connected to patient care device 312 through one or more auxiliary interfaces 362.

Each functional module 316, 318, 320, 322 may include module-specific components 376, a microprocessor 370, a volatile memory 372 and a nonvolatile memory 374 for storing information. It should be noted that while four functional modules are shown in FIG. 3, any number of devices may be connected directly or indirectly to central controller 314. The number and type of functional modules described herein are intended to be illustrative, and in no way limit the scope of the subject technology. Module-specific components 376 include any components necessary for operation of a particular module, such as a pumping mechanism for infusion pump module 316.

While each functional module may be capable of a least some level of independent operation, interface unit 314 monitors and controls overall operation of device 312. For example, as will be described in more detail below, interface unit 314 provides programming instructions to the functional modules 316, 318, 320, 322 and monitors the status of each module.

Patient care device 312 is capable of operating in several different modes, or personalities, with each personality defined by a configuration database. The configuration database may be a database 356 internal to patient care device, or an external database 337. A particular configuration database is selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a patient care device's 312 location in the hospital or hospital computer network. Patient care information may be entered through interface device 354, or the data input device 360, or auxiliary interface 362, and may originate from anywhere in network 310, such as, for example, from a pharmacy server, admissions server, laboratory server, and the like.

Medical devices incorporating aspects of the subject technology may be equipped with a Network Interface Module (NIM), allowing the medical device to participate as a node in a network. While for purposes of clarity the subject technology will be described as operating in an Ethernet network environment using the Internet Protocol (IP), it is understood that concepts of the subject technology are equally applicable in other network environments, and such environments are intended to be within the scope of the subject technology.

Data to and from the various data sources can be converted into network-compatible data with existing technology, and movement of the information between the medical device and network can be accomplished by a variety of means. For example, patient care device 312 and network 310 may communicate via automated interaction, manual interaction or a combination of both automated and manual interaction. Automated interaction may be continuous or intermittent and may occur through direct network connection 352 (as shown in FIG. 3), or through RS232 links, MIB systems, RF links such as BLUETOOTH, IR links, WLANS, digital cable systems, telephone modems or other wired or wireless communication means. Manual interaction between patient care device 312 and network 310 involves physically transferring, intermittently or periodically, data between systems using, for example, user interface device 354, coded data input device 360, bar codes, computer disks, portable data assistants, memory cards, or any other media for storing data. The communication means in various aspects is bidirectional with access to data from as many points of the distributed data sources as possible. Decision-making can occur at a variety of places within network 310. For example, and not by way of limitation, decisions can be made in a remote data server, a hospital department or unit stations, or within patient care device 312 itself.

All direct communications with medical devices operating on a network in accordance with the subject technology may be performed through information system server 30, known as the remote data server (RDS). In accordance with aspects of the subject technology, network interface modules incorporated into medical devices such as, for example, infusion pumps or vital signs measurement devices, ignore all network traffic that does not originate from an authenticated RDS. The primary responsibilities of the RDS of the subject technology are to track the location and status of all networked medical devices, and maintain open communication.

With further reference to FIG. 9, an infusion device, as used herein, may be a patient care device 312, interface control unit 314, or a module 316, 318, 320, 322. According to various implementations, the infusion device includes a pump and a control unit. The control unit 314 is configured to provide, using the pump, an intravenous infusion of a medication to a current patient, and display on a display screen, while the infusion is being provided by the pump, a representation of a status of the intravenous infusion. The representation of the status may include, for example, a single colored light emanating from an LED affixed to the control unit, pump, or infusion device generally, or may be an element displayed on the display screen. In some implementations, the colored light bay be a backlight or lighted outline around content in a display screen.

Control unit 314 is configured to send, during the infusion, to a remote records system 330, infusion information including a patient identifier and order identifier for the infusion currently being provided by the pump. For example, a caregiver may input that a particular patient is receiving a certain dose of acyclovir, and the patient ID, drug ID, and dosage information may be sent to system 330 along with the device ID of the infusion device. Records system 330 may then send to control unit 314 (for which control unit 314 is configured to then receive), a confirmation of the infusion information and any limits for the medication and or the patient based on the information received, as described previously.

Figure 10:
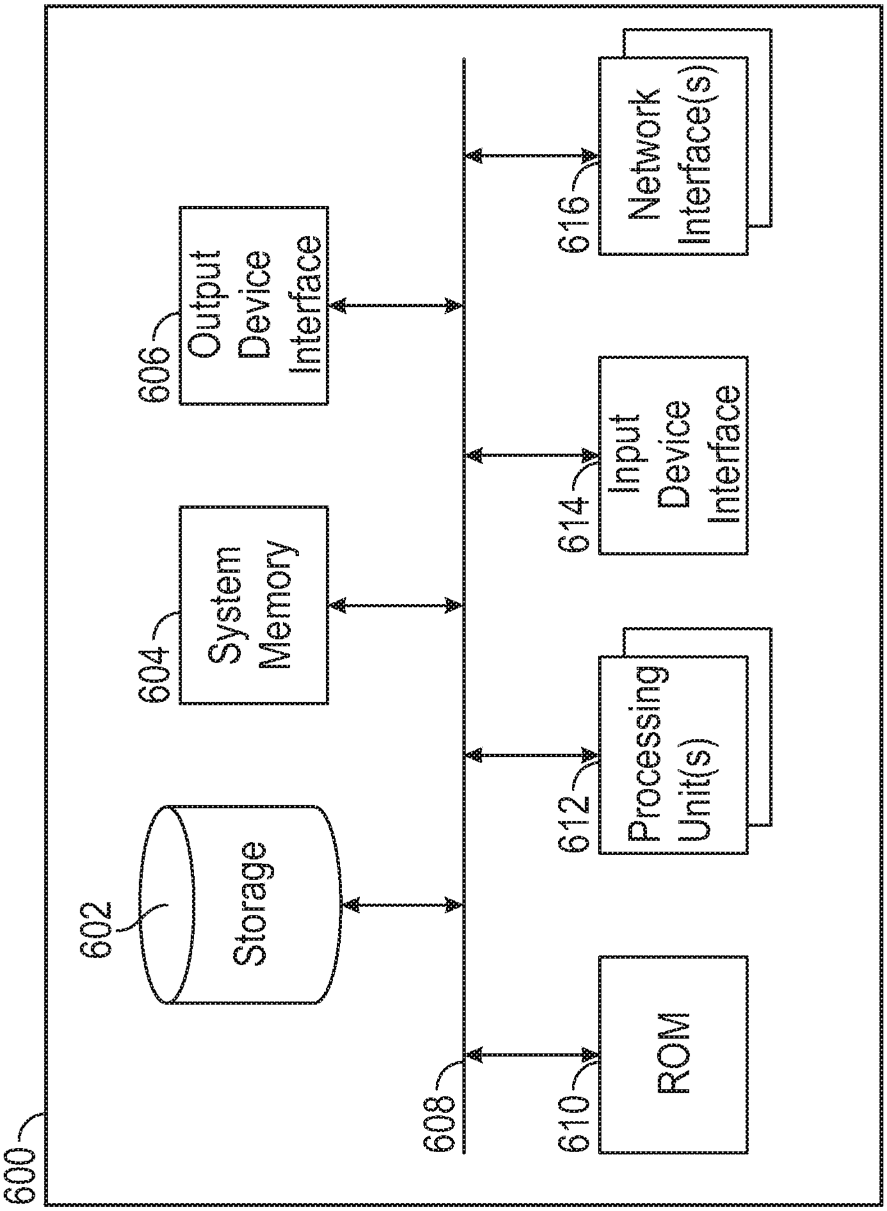
FIG. 10 is a conceptual diagram illustrating an example electronic system for programming an infusion device, according to aspects of the subject technology.

FIG. 10 is a conceptual diagram illustrating an example electronic system 400 for programming an infusion device, according to aspects of the subject technology. Electronic system 600 may be a computing device for execution of software associated with one or more components and processes provided by FIGS. 1 to 9, including but not limited to infusion device 1, 312 or system 330, or computing hardware within infusion device 1, 312 or system 330. Electronic system 600 may include a personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 600 may include various types of computer readable media and interfaces for various other types of computer readable media. In the depicted example, electronic system 600 includes a bus 608, processing unit(s) 612, a system memory 604, a read-only memory (ROM) 610, a permanent storage device 602, an input device interface 614, an output device interface 606, and one or more network interfaces 616. In some implementations, electronic system 600 may include or be integrated with other computing devices or circuitry for operation of the various components and processes previously described.

Bus 608 collectively represents all system, peripheral, and chipset buses that communicatively connect the numerous internal devices of electronic system 600. For instance, bus 608 communicatively connects processing unit(s) 612 with ROM 610, system memory 604, and permanent storage device 602.

From these various memory units, processing unit(s) 612 retrieves instructions to execute and data to process in order to execute the processes of the subject disclosure. The processing unit(s) can be a single processor or a multi-core processor in different implementations.

ROM 610 stores static data and instructions that are needed by processing unit(s) 612 and other modules of the electronic system. Permanent storage device 602, on the other hand, is a read-and-write memory device. This device is a non-volatile memory unit that stores instructions and data even when electronic system 600 is off. Some implementations of the subject disclosure use a mass-storage device (such as a magnetic or optical disk and its corresponding disk drive) as permanent storage device 602.

Other implementations use a removable storage device (such as a floppy disk, flash drive, and its corresponding disk drive) as permanent storage device 602. Like permanent storage device 602, system memory 604 is a read-and-write memory device. However, unlike storage device 602, system memory 604 is a volatile read-and-write memory, such a random access memory. System memory 604 stores some of the instructions and data that the processor needs at runtime. In some implementations, the processes of the subject disclosure are stored in system memory 604, permanent storage device 602, and/or ROM 610. From these various memory units, processing unit(s) 612 retrieves instructions to execute and data to process in order to execute the processes of some implementations.

Bus 608 also connects to input and output device interfaces 614 and 606. Input device interface 614 enables the user to communicate information and select commands to the electronic system. Input devices used with input device interface 614 include, e.g., alphanumeric keyboards and pointing devices (also called "cursor control devices"). Output device interfaces 606 enables, e.g., the display of images generated by the electronic system 600. Output devices used with output device interface 606 include, e.g., printers and display devices, such as cathode ray tubes (CRT) or liquid crystal displays (LCD). Some implementations include devices such as a touchscreen that functions as both input and output devices.

Also, as shown in FIG. 6, bus 608 also couples electronic system 600 to a network (not shown) through network interfaces 616. Network interfaces 616 may include, e.g., a wireless access point (e.g., Bluetooth or WiFi) or radio circuitry for connecting to a wireless access point. Network interfaces 616 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 600 can be used in conjunction with the subject disclosure.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (also referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

The previous description is provided to enable a person of ordinary skill in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identification.

Clause 1. An infusion device, comprising: a processor; a memory device; and a display screen; wherein the processor is configured to: determine a medication loaded by the infusion device, determine, based on determining the medication, a number of digit fields for inputting a parameter associated with the determined medication, query a dataset for limits pertaining to the medication; obtain, from the dataset based on the querying, a first limit and a second limit pertaining to the medication; determine which of the digit fields are selectable based on the first limit; display, on the display screen of the infusion device, a plurality of selectable character input fields corresponding to the number of digit fields determined to be selectable; visually identify, on the display screen, a first character input field of the displayed selectable character input fields as an adjustable field; display, on the display screen, one or more controls for incrementing or decrementing a value of the identified adjustable field, each control configured to only increment or decrement the value of the identified adjustable field; receive a selection of a second character input field of the displayed selectable character input fields; visually identify, on the display screen, responsive to receiving the selection, the second character input field as the adjustable field; adjust a value of the selected second character input field based on an activation of the one or more controls while the second character input field is selected as the adjustable field; determine that the adjusted value of the second character input field exceeded the second limit; and in response to determining that the adjusted value exceeded the second limit, display an alert, indicating the adjusted value exceeded the second limit, proximate to the adjusted value of the second selectable character input field.

Clause 2. The infusion device of Clause 1, wherein the processor is further configured to: provide for display on the display screen a control for adding a decimal character to the plurality of selectable character input fields; receive a selection of the second control; after receiving the selection of the second control: determine a decimal location for the decimal character based on the determined medication; cause a new character input field to be displayed on the display screen to represent a value less than a whole unit; and cause the decimal character to be displayed at the determined decimal location between the first character input field and the new character input field.

Clause 3. The infusion device of Clause 1 or Clause 2, wherein determining the number of digit fields includes automatically determining a decimal location between the plurality of selectable character input fields based on the determined medication and displaying a decimal character at the determined decimal location.

Clause 4. The infusion device of any one of Clauses 1 through 3, wherein the value of the selected second character input field is greater than a value of the first character input field by a magnitude of ten, and the first and second character input fields are null prior to the selected second character input field being adjusted, and wherein adjusting the value of the second character input field comprises setting the second character input field to "1" and the first character input field to "0", wherein the value of the second character input field is incremented responsive to each subsequent selection of activation of the one or more controls up until the first limit, after which each subsequent selection increments the first character input field up until the second limit, the second limit being greater than the first limit.

Clause 5. The infusion device of any one of Clauses 1 through 4, wherein the processor is further configured to: change a background color of the display screen responsive to obtaining the first limit and the second limit.

Clause 6. The infusion device of any one of Clauses 1 through 5, wherein the processor is further configured to: display, proximate to the plurality of selectable character input fields, a graphical representation of a parameter range corresponding to the second limit.

Clause 7. The infusion device of any one of Clauses 1 through 6, wherein visually identifying the adjustable input field comprises highlighting an area enclosing only the adjustable input field.

Clause 8. The infusion device of Clause 7, wherein the processor is further configured to: receive an adjustment of a current value of the adjustable input field to a higher value; and after the adjusted current value exceeding a threshold for a display of a single digit representation of the adjusted current value, expand the highlighted area to enclose the adjustable input field and an adjacent input field of the displayed selectable character input fields to represent the adjusted current value.

Clause 9. The infusion device of Clause 8, wherein the processor is further configured to: receive an adjustment of the adjusted current value of the adjustable input field to a lower value; and after the adjusted current value being reduced below the threshold for the display of the single digit representation, revert the highlighted area to enclose only the adjustable input field.

Clause 10. The infusion device of any one of Clauses 7 through 9, wherein the processor is further configured to: monitor the one or more controls; and flash the highlighted area responsive to not detecting an activation of the one or more controls after a predetermined period of time.

Clause 11. A method, comprising: determining a medication loaded by an infusion device; determining, based on determining the medication, a number of digit fields for inputting a parameter associated with the determined medication; querying a dataset for limits pertaining to the medication; obtaining, from the dataset based on the querying, a first limit and a second limit pertaining to the medication; determining which of the digit fields are selectable based on the first limit; displaying, on the display screen of the infusion device, a plurality of selectable character input fields corresponding to the number of digit fields determined to be selectable; visually identifying, on the display screen, a first character input field of the displayed selectable character input fields as an adjustable field; displaying, on the display screen, one or more controls for incrementing or decrementing a value of the identified adjustable field, each control configured to only increment or decrement the value of the identified adjustable field; receiving a selection of a second character input field of the displayed selectable character input fields; visually identifying, on the display screen, responsive to receiving the selection, the second character input field as the adjustable field; adjusting a value of the selected second character input field based on an activation of the one or more controls while the second character input field is selected as the adjustable field; determining that the adjusted value of the second character input field exceeded the second limit; and in response to determining that the adjusted value exceeded the second limit, displaying an alert, indicating the adjusted value exceeded the second limit, proximate to the adjusted value of the second selectable character input field.

Clause 12. The method of Clause 11, further comprising: providing for display on the display screen a control for adding a decimal character to the plurality of selectable character input fields; receiving a selection of the second control; after receiving the selection of the second control: determining a decimal location for the decimal character based on the determined medication; causing a new character input field to be displayed on the display screen to represent a value less than a whole unit; and causing the decimal character to be displayed at the determined decimal location between the first character input field and the new character input field.

Clause 13. The method of any one of Clause 11 or Clause 12, wherein determining the number of digit fields includes automatically determining a decimal location between the plurality of selectable character input fields based on the determined medication and displaying a decimal character at the determined decimal location.

Clause 14. The method of any one of Clauses 11 through 13, wherein the value of the selected second character input field is greater than a value of the first character input field by a magnitude of ten, and the first and second character input fields are null prior to the selected second character input field being adjusted, and wherein adjusting the value of the second character input field comprises setting the second character input field to "1" and the first character input field to "0", wherein the value of the second character input field is incremented responsive to each subsequent selection of activation of the one or more controls up until the first limit, after which each subsequent selection increments the first character input field up until the second limit, the second limit being greater than the first limit.

Clause 15. The method of any one of Clauses 11 through 14, further comprising: changing a background color of the display screen responsive to obtaining the first limit and the second limit, wherein the alert is displayed underneath and aligned with the adjusted value of the second character input field.

Clause 16. The method of any one of Clauses 11 through 15, further comprising: displaying, proximate to the plurality of selectable character input fields, a graphical representation of a parameter range corresponding to the second limit.

Clause 17. The method of any one of Clauses 11 through 16, wherein visually identifying the adjustable input field comprises highlighting an area enclosing only the adjustable input field.

Clause 18. The method of Clause 17, further comprising: receiving an adjustment of a current value of the adjustable input field to a higher value; and responsive to the adjusted current value exceeding a threshold for a display of a single digit representation of the adjusted current value, expanding the highlighted area to enclose the adjustable input field and an adjacent input field of the displayed selectable character input fields to represent the adjusted current value.

Clause 19. The method of Clause 18, further comprising: receiving an adjustment of the adjusted current value of the adjustable input field to a lower value; and after the adjusted current value being reduced below the threshold for the display of the single digit representation, reverting the highlighted area to enclose only the adjustable input field.

Clause 20. The method of Clause 17, further comprising: monitoring the one or more controls; and flashing the highlighted area responsive to not detecting an activation of the one or more controls after a predetermined period of time.

Clause 21. A non-transitory machine readable medium storing instructions thereon that, when executed by a machine or computing device, cause the machine or computing device to perform a method according to any one of Clauses 11 through 20.

Further Consideration

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit this disclosure.

The predicate words "configured to," "operable to," and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

As used herein, a "key" that can be pressed may be implemented as an interactive element on a device that specifically causes the identified response or a general purpose interactive element that, depending on operational state of the device, causes the identified response. In some implementations, the interactive element may be an electromechanical element (e.g., button or switch) to generate a signal or message. In some implementations, the interactive element may be a virtual element presented on a graphical user interface (e.g., button, slider, etc.) that, when interacted with, generates a signal or message.

All structural and functional equivalents to the elements of the various aspects described throughout this disclosure that are known or later come to be known to those of ordinary skill in the art are expressly incorporated herein by reference and are intended to be encompassed by any claim. Furthermore, to the extent that the term "include," "have," or the like is used in the description, such term is intended to be inclusive in a manner similar to the term "comprise" as "comprise" is interpreted when employed as a transitional word.

What is claimed is:

1. An infusion device, comprising:

a processor;

a memory device; and a display screen;

wherein the processor is configured to:

determine a medication loaded by the infusion device;

determine, based on determining the medication, a number of digit fields for inputting a parameter associated with the determined medication;

query a dataset for limits pertaining to the medication;

obtain, from the dataset based on the querying, a first limit and a second limit pertaining to the medication;

determine which of the digit fields are selectable based on the first limit;

display, on the display screen of the infusion device, a plurality of selectable character input fields corresponding to the number of digit fields determined to be selectable;

visually identify, on the display screen, a first character input field of the displayed selectable character input fields as an adjustable field;

display, on the display screen, one or more controls for incrementing or decrementing a value of the identified adjustable field, each control configured to only increment or decrement the value of the identified adjustable field;

receive a selection of a second character input field of the displayed selectable character input fields;

visually identify, on the display screen, responsive to receiving the selection, the second character input field as the adjustable field;

adjust a value of the selected second character input field based on an activation of the one or more controls while the second character input field is selected as the adjustable field;

determine that the adjusted value of the second character input field exceeded the second limit; and in response to determining that the adjusted value exceeded the second limit, display an alert, indicating the adjusted value exceeded the second limit, proximate to the adjusted value of the second selectable character input field.

2. The infusion device of claim 1, wherein the processor is further configured to:

provide for display on the display screen a control for adding a decimal character to the plurality of selectable character input fields;

receive a selection of the second control;

after receiving the selection of the second control:

determine a decimal location for the decimal character based on the determined medication;

cause a new character input field to be displayed on the display screen to represent a value less than a whole unit; and cause the decimal character to be displayed at the determined decimal location between the first character input field and the new character input field.

3. The infusion device of claim 1, wherein determining the number of digit fields includes automatically determining a decimal location between the plurality of selectable character input fields based on the determined medication and displaying a decimal character at the determined decimal location.

4. The infusion device of claim 1, wherein the value of the selected second character input field is greater than a value of the first character input field by a magnitude of ten, and the first and second character input fields are null prior to the selected second character input field being adjusted, and wherein adjusting the value of the second character input field comprises setting the second character input field to "1" and the first character input field to "0", wherein the value of the second character input field is incremented responsive to each subsequent selection of activation of the one or more controls up until the first limit, after which each subsequent selection increments the first character input field up until the second limit, the second limit being greater than the first limit.

5. The infusion device of claim 1, wherein the processor is further configured to:

change a background color of the display screen responsive to obtaining the first limit and the second limit.

6. The infusion device of claim 1, wherein the processor is further configured to:

display, proximate to the plurality of selectable character input fields, a graphical representation of a parameter range corresponding to the second limit.

7. The infusion device of claim 1, wherein visually identifying the adjustable input field comprises highlighting an area enclosing only the adjustable input field.

8. The infusion device of claim 7, wherein the processor is further configured to:

receive an adjustment of a current value of the adjustable input field to a higher value; and after the adjusted current value exceeding a threshold for a display of a single digit representation of the adjusted current value, expand the highlighted area to enclose the adjustable input field and an adjacent input field of the displayed selectable character input fields to represent the adjusted current value.

9. The infusion device of claim 8, wherein the processor is further configured to:

receive an adjustment of the adjusted current value of the adjustable input field to a lower value; and after the adjusted current value being reduced below the threshold for the display of the single digit representation, revert the highlighted area to enclose only the adjustable input field.

10. The infusion device of claim 7, wherein the processor is further configured to:

monitor the one or more controls; and flash the highlighted area responsive to not detecting an activation of the one or more controls after a predetermined period of time.

11. A method, comprising:

determining a medication loaded by an infusion device;

determining, based on determining the medication, a number of digit fields for inputting a parameter associated with the determined medication;

querying a dataset for limits pertaining to the medication;

obtaining, from the dataset based on the querying, a first limit and a second limit pertaining to the medication;

determining which of the digit fields are selectable based on the first limit;

displaying, on the display screen of the infusion device, a plurality of selectable character input fields corresponding to the number of digit fields determined to be selectable;

visually identifying, on the display screen, a first character input field of the displayed selectable character input fields as an adjustable field;

displaying, on the display screen, one or more controls for incrementing or decrementing a value of the identified adjustable field, each control configured to only increment or decrement the value of the identified adjustable field;

receiving a selection of a second character input field of the displayed selectable character input fields;

visually identifying, on the display screen, responsive to receiving the selection, the second character input field as the adjustable field;

adjusting a value of the selected second character input field based on an activation of the one or more controls while the second character input field is selected as the adjustable field;

determining that the adjusted value of the second character input field exceeded the second limit; and in response to determining that the adjusted value exceeded the second limit, displaying an alert, indicating the adjusted value exceeded the second limit, proximate to the adjusted value of the second selectable character input field.

12. The method of claim 11, further comprising:

providing for display on the display screen a control for adding a decimal character to the plurality of selectable character input fields;

receiving a selection of the second control;

after receiving the selection of the second control:

determining a decimal location for the decimal character based on the determined medication;

causing a new character input field to be displayed on the display screen to represent a value less than a whole unit; and causing the decimal character to be displayed at the determined decimal location between the first character input field and the new character input field.

13. The method of claim 11, wherein determining the number of digit fields includes automatically determining a decimal location between the plurality of selectable character input fields based on the determined medication and displaying a decimal character at the determined decimal location.

14. The method of claim 11, wherein the value of the selected second character input field is greater than a value of the first character input field by a magnitude of ten, and the first and second character input fields are null prior to the selected second character input field being adjusted, and wherein adjusting the value of the second character input field comprises setting the second character input field to “1” and the first character input field to “0”, wherein the value of the second character input field is incremented responsive to each subsequent selection of activation of the one or more controls up until the first limit, after which each subsequent selection increments the first character input field up until the second limit, the second limit being greater than the first limit.

15. The method of claim 11, further comprising:

changing a background color of the display screen responsive to obtaining the first limit and the second limit, wherein the alert is displayed underneath and aligned with the adjusted value of the second character input field.

16. The method of claim 11, further comprising:

displaying, proximate to the plurality of selectable character input fields, a graphical representation of a parameter range corresponding to the second limit.

17. The method of claim 11, wherein visually identifying the adjustable input field comprises highlighting an area enclosing only the adjustable input field.

18. The method of claim 17, further comprising:

receiving an adjustment of a current value of the adjustable input field to a higher value; and responsive to the adjusted current value exceeding a threshold for a display of a single digit representation of the adjusted current value, expanding the highlighted area to enclose the adjustable input field and an adjacent input field of the displayed selectable character input fields to represent the adjusted current value.

19. The method of claim 18, further comprising:

receiving an adjustment of the adjusted current value of the adjustable input field to a lower value; and after the adjusted current value being reduced below the threshold for the display of the single digit representation, reverting the highlighted area to enclose only the adjustable input field.

20. The method of claim 17, further comprising:

monitoring the one or more controls; and flashing the highlighted area responsive to not detecting an activation of the one or more controls after a predetermined period of time.

* * * * *